(12) United States Patent
Harper et al.

(10) Patent No.: US 11,975,090 B2
(45) Date of Patent: May 7, 2024

(54) SULFATE-FREE, FOAMABLE SOLID CLEANSER COMPRISING AN ISETHIONATE/BETAINE SURFACTANT SYSTEM

(71) Applicant: Johnson & Johnson Consumer Inc., Skillman, NJ (US)

(72) Inventors: Donald L. Harper, Flemington, NJ (US); Marcee Martinez, Cedar Knolls, NJ (US); Shailendra Singh, Monroe Township, NJ (US)

(73) Assignee: Johnson & Johnson Consumer Inc., Skillman, NJ (US)

( * ) Notice: Subject to any disclaimer, the term of this patent is extended or adjusted under 35 U.S.C. 154(b) by 595 days.

(21) Appl. No.: 16/668,718

(22) Filed: Oct. 30, 2019

(65) Prior Publication Data
US 2021/0128435 A1 May 6, 2021

(51) Int. Cl.
| | | |
|---|---|---|
| *C11D 1/94* | (2006.01) | |
| *A61K 8/02* | (2006.01) | |
| *A61K 8/04* | (2006.01) | |
| *A61K 8/19* | (2006.01) | |
| *A61K 8/365* | (2006.01) | |
| *A61K 8/44* | (2006.01) | |
| *A61K 8/46* | (2006.01) | |
| *A61Q 19/10* | (2006.01) | |
| *C11D 1/12* | (2006.01) | |
| *C11D 1/90* | (2006.01) | |

(52) U.S. Cl.
CPC ............ *A61K 8/466* (2013.01); *A61K 8/0225* (2013.01); *A61K 8/046* (2013.01); *A61K 8/19* (2013.01); *A61K 8/365* (2013.01); *A61K 8/442* (2013.01); *A61K 8/447* (2013.01); *A61Q 19/10* (2013.01); *C11D 1/126* (2013.01); *C11D 1/90* (2013.01); *A61K 2800/596* (2013.01)

(58) Field of Classification Search
CPC .. C11D 1/126; C11D 1/90; C11D 1/94; C11D 3/10; C11D 3/126; C11D 7/12; C11D 9/12; C11D 17/044
See application file for complete search history.

(56) References Cited

U.S. PATENT DOCUMENTS

| | | | | |
|---|---|---|---|---|
| 5,910,475 A | * | 6/1999 | Neumiller | C11D 3/2096 510/192 |
| 6,310,014 B1 | * | 10/2001 | Rau | C11D 3/221 510/276 |
| 6,506,713 B1 | * | 1/2003 | Slavtcheff | A61K 8/365 424/404 |
| 2003/0080150 A1 | | 5/2003 | Cowan | |
| 2005/0288208 A1 | * | 12/2005 | Keenan | C11D 3/3769 510/439 |
| 2006/0162139 A1 | * | 7/2006 | Bergquist | B32B 27/32 28/105 |
| 2018/0153777 A1 | * | 6/2018 | De Luigi | A61K 8/0245 |
| 2018/0235866 A1 | * | 8/2018 | Constantine | A61K 8/922 |
| 2018/0318195 A1 | | 11/2018 | Blachechen et al. | |
| 2019/0282837 A1 | * | 9/2019 | Sheirs | C11D 3/222 |
| 2020/0190446 A1 | * | 6/2020 | Sivik | D04H 3/007 |
| 2020/0405605 A1 | * | 12/2020 | Wei | A61K 8/0208 |

FOREIGN PATENT DOCUMENTS

| | | | |
|---|---|---|---|
| CA | 2459164 | * | 1/2004 |
| CN | 106350328 A | | 1/2017 |
| DE | 19745964 A1 | | 6/1998 |
| EP | 3241885 A1 | | 11/2017 |
| KR | 2015108663 A | | 9/2015 |
| KR | 2018094238 A | | 8/2018 |
| RU | 2266317 C2 | | 12/2005 |
| RU | 2605268 C2 | | 12/2016 |
| WO | WO2000007561 A1 | | 2/2000 |
| WO | WO 01/56542 A1 | | 8/2001 |
| WO | WO2001028513 A3 | | 11/2001 |
| WO | WO2003/022230 | | 3/2003 |
| WO | WO 2019/001940 A1 | | 1/2019 |

OTHER PUBLICATIONS

PCT Search Report for corresponding International Application No. PCT/B2019/059317 dated Jul. 1, 2020.
Database GNPD [online] MINTEL; Mar. 29, 2018, anonymous: "Unicorn Fizzy Donut", XP055649942, retrieved from www.gnpd.com Database accession No. 5553819.
Database GNPD [online] MINTEL; May 22, 2017, anonymous: "Foaming Bath Salts", XP055649932, retrieved from www.gnpd.com Database accession No. 4831081.
Database GNPD [online] MINTEL; Sep. 18, 2009, anonymous: "Skin Softening Bath Salts", XP055649822, retrieved from www.gnpd.com Database accession No. 1176860.
Written Opinion of the International Searching Authority for corresponding International Application No. PCT/B2019/059317 dated Jul. 13, 2020.
Nikolaev P.V. "Osnovy himii i tehnologii proizvodstva sintetičeskih moûŝih sredstv: Učebnoeposobie" [*Fundamentals of Chemistry and Technology of Synthetic Detergents: Textbook*] /p. V. Nikolaaev, N.A. Kozlov, S.N. Petrova; Ivanovo State University of Chemistry and Technology, Ivanovo, 2007, pp. 11-56.

(Continued)

*Primary Examiner* — Charles I Boyer
(74) *Attorney, Agent, or Firm* — Rachel Chaves

(57) ABSTRACT

A solid cleansing product including at least a first surfactant and a second surfactant present in a combined surfactant weight amount, both of the first and second surfactants being free of sulfate-containing materials; at least a first buffering agent and a second buffering agent a present in a combined buffering agent weight amount; where the combined buffering agent weight amount is at least double the combined surfactant weight amount.

15 Claims, 4 Drawing Sheets

(56) References Cited

OTHER PUBLICATIONS

Tihomirov V.K. "Peny. Teoriâ i praktika ih polučeniâ i razruŝehiâ" [*Foams. Theory and practice of their production and destruction*], M., "Himiâ", 1975, pp. 18-19, 22.

Âkov Ivanovič Gerasimov et al. "Kurs fizičeskoj himii" [*Course of Physical Chemistry*], vol. 11, Publishing house "Himia", M.—1966, p. 494, 492).

WayBackMachine (web.archive.org): http://www.reachdevices.com/Protein/BiologicalBuffers.html.

Bashkir State University, Kurs lekcij: Tehnologiâ proizvodstva poverhnostno-aktivnyh veŝestv[*Course of lectures: Technology of surfactants production*], 2018, https://spravochnick.ru/lektoriy/tehnologiya-proizvodstva-poverhnostno-aktivnyhveschestv/.

Wikipedia [https://translated.turbopages.org/proxy_u/en-ru.ru.004b5110-64269b9f-439c58ef-74722d776562/https/en.wikipedia.org/wiki/Buffering_agent.

https://ru.abcdef.wiki/wiki/Buffering_agent?ysclid=lmeuxhxc9l619668629 https://spravochnick.ru/lektoriy/technologiya-proizvodstva-poverhnostno-aktivnyh-veschestv/.

\* cited by examiner

SULFATE-FREE, FOAMABLE SOLID CLEANSER COMPRISING AN ISETHIONATE/BETAINE SURFACTANT SYSTEM

FIELD

The present invention relates to cleansing products, and in particular solid cleansing products. The solid cleansing products are at least substantially free of sulfates, are foamable in the presence of a fluid, such as water, and in some aspects may be in the form of a loose powder, a capsule, or a pressed tablet.

BACKGROUND

Cleansing products come in various forms, including liquid forms. Liquid cleansing forms are quite useful and effective, but they are susceptible to leaks and spills, and also typically require larger packages, such as bottles. For this reason, a solid cleansing product may be desired. Solid cleansing products are dissolvable in the presence of a fluid. Solid cleansers, however, do not often foam to a desired profile or volume, that is, they do not foam quickly enough, nor do they have the desired foam stability. It is particularly desired that a solid cleanser not turn into a "paste" when exposed to water and used on the skin of the user, rather, a soft foamy texture is desired.

"Bath Bombs" are products that are generally solid in nature and dissolve in the presence of water, where the bath bomb includes a cleansing product contained therein. Bath Bombs are generally hard-packed mixtures of dry ingredients that effervesce when wetted. These products generally react vigorously in the presence of water to provide a fizzing and complete dissolution within less than 5 minutes. Bath bombs are known to provide one or more elements to bath water, such as fragrance, oils, bubbles or colors. However, bath bombs typically do not provide a desired foaming profile or volume when used, nor do they provide any moisturizing effect or other skin benefits, in particular, facial benefits, such as acne treatment. Bath bombs are typically used to provide elements to a large body of water (such as a full bathtub), but not to provide foamed cleansing to a user. Bath bombs are typically not suitable for dissolution in the hands of a user and subsequently used on the skin or face of the user.

There is a need for a solid cleansing product, particularly one made from powdered materials and which are free of sulfate-containing components, which are sufficiently mild to use on the skin of the user, and which provides a combination of rapid foaming, cleansing, moisturizing and skin conditioning ingredients. The present invention provides a solid cleansing product, which has a desirable volume of foam generated within a desired time, and further has a desirable foam stability, as well as providing desired cleansing levels. The solid cleansing products may be in the form of concentrated cleansing tablets, which transform into a bubbly, cushy foam at a rapid pace to give a desired level of cleansing without harshness, dryness or irritation to the user's skin. Certain embodiments of the solid cleansing product may also include moisturizing agents to leave user's skin feeling moisturized.

DETAILED DESCRIPTION

Figure 1:
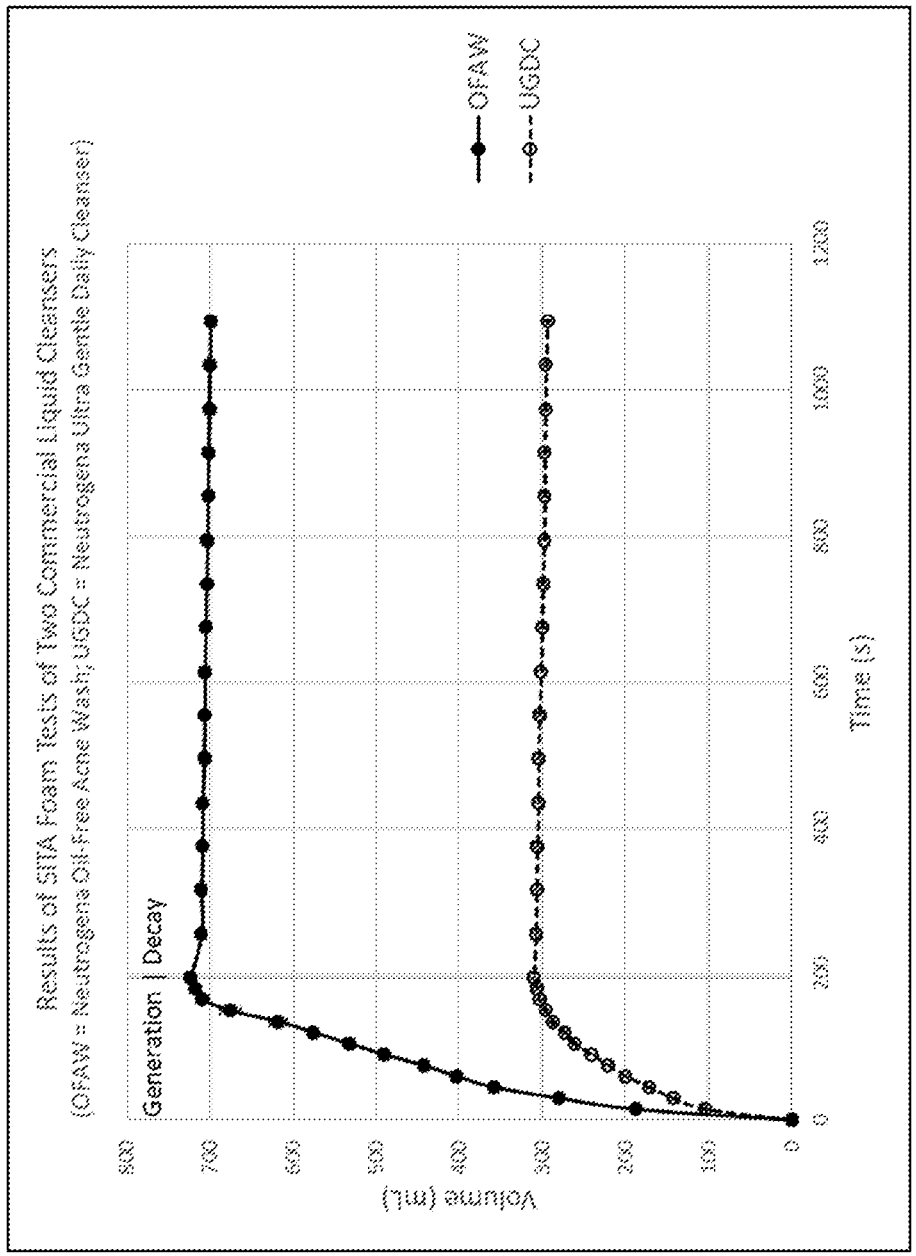
FIG. 1 is a graph depicting the results of foam tests for two commercial liquid cleansers.

As used herein, the term "solid" refers to a material that is not in liquid form. Solid products may include flowable granules or powders, or may include a larger solid form, such as a tablet or pressed tablet. Desirably, solid products as described herein are anhydrous in nature. It is desired that the cleansing products herein be substantially free of added water, and is more desired that the cleansing products herein be free of added water. The term "substantially free of added water" means that the cleansing product contain less than 0.1% of added water, more desirably less than 0.01% of added water. The cleansing products that are free of added water may include trace levels of water due to the presence of water in ingredients such as fragrances, extracts, and the like, as well as due to the presence of moisture in the air, however, the amount of trace water in the cleansing products should be less than 0.1% by weight of the formulation, more desirably less than 0.1% by weight of the formulation, and more desirably less than 0.01% by weight of the formulation.

The cleansing product described herein may be in one of a number of different forms. It may be in the form of a pressed tablet, as will be described in greater detail below. The cleansing product may be a powdered material in a sachet, capsule, or other storage unit. The cleansing product may be encapsulated in an outer capsule or other shell, may be encapsulated within an outer dissolvable film or casing, where the outer material may be either separated or broken to release the cleansing product, or dissolved during use, thereby releasing the cleansing components contained therein. In some aspects, the cleansing product is a granulated or powdered material, which may be dispensed from a storage container prior to use.

It is most desired that the components of the cleansing product be solid, such as in the form of a powder or granules. Most desirably, the components are in the form of powders or granules, and if desired, the components may be subjected to a milling or rolling step prior to the formation of the cleansing product. As used herein, the term "powder" refers to a particulate material having an average cross-sectional diameter of less than about 2.1 microns, or less than about 1.1 microns, or less than about 0.8 microns. It is noted that the term "diameter" does not necessarily require that the particle be spherical in shape, and can refer to particles having any cross-sectional configuration.

Compositions and products of the present invention are at least substantially free from components that include sulfates, and in preferred embodiments are free from sulfate-containing components. As used herein, the term "at least substantially free" refers to a composition which contains less than 0.1% by weight of a sulfate-containing component, and more preferably which contains less than 0.01% by weight of a sulfate-containing component.

The cleansing product includes a number of components, including at least one surfactant. Desirably, the cleansing product includes at least two surfactants, where the first and second surfactants differ from each other. The cleansing product may also include at least one skin conditioning agent, such as shea butter (or alternatively shea butter powder including a blend of shea butter in a silica carrier, sold as Jarplex SB60 by Jarchem Industries Inc.). The cleansing product may also include a buffering agent. The cleansing product also includes a binder, and may optionally include a bulking agent. In desired embodiments, the cleansing product includes a glidant, such as silica, which aids in processing. The cleansing product may also include an anticaking agent. Optionally, the cleansing product may include a skin benefit agent such as an anti-acne agent, anti-aging agents, antimicrobial agents, and the like.

Cleansing products may also include other additives such as colors or fragrances, if desired.

As noted above, cleansing product includes at least one surfactant, and desirably includes more than one surfactant, where the first and second surfactants are different from each other. Surfactants useful in the present invention include anionic such as sodium cocoyl isethionate, sodium lauroyl sarcosinate, cocamidopropyl betaine, sodium dioctyl sulfosuccinate, sodium methyl cocoyl taurate, and acyl isethionates. Preferably, the first surfactant is sodium cocoyl isethionate. Other surfactants useful in the present invention include cationic surfactants, such as quaternary ammonium salts, amine oxides, and ester quats; amphoteric surfactants, such as betaines, amidobetaines, ester betaines, and amphoacetates; and nonionic surfactants, such as alky polyglycosides, alcohol ethoxylates, and fatty alkanol amides. In embodiments where there is more than one surfactant, the first surfactant and second surfactant may both be the anionic, nonionic, cationic, or amphoteric, or the first and second surfactants may be different in ionic nature.

Surfactants may be present in any amount from about 1% to about 50% by weight of the overall product, or may be present in an amount from about 5% to about 40% by weight of the overall product, or may be present in an amount of from about 10% to about 30% by weight of the overall product. If more than one surfactant is used, each surfactant may be present in the same weight amount or may be present in different weight amounts. The first surfactant and second surfactant may be present in weight ratios of from 1:1 to 10:1, or from 1:1 to 5:1, or from 1:1 to 3:1, or from 1:1 to about 1:1.5, respectively. Preferably, the first surfactant and second surfactant may be present in weight ratios of about 1:1.

Binding agents useful in the present invention include, but not limited to lactose, methyl cellulose, hydroxypropyl cellulose, hydroxypropylmethyl cellulose, gelatin, gum arabic, ethyl cellulose, polyvinyl alcohol, pullulan, pregelatinized starch, agar, tragacanth, sodium alginate, propyleneglycol alginate, and the like. One such binding agent is lactose monohydrate, while other binding agents include microcrystalline cellulose, and pregelatinized starch. One such microcrystalline cellulose that may be used in the invention includes a silicified microcrystalline cellulose sold under the name ProSolv SMCC (sold by JRS Pharma). ProSolv SMCC is a combination of microcrystalline cellulose and colloidal silicon dioxide, and may be available with an average particle size of from 50 to 65 micrometers (ProSolv SMCC 50 and ProSolv SMCC 50 LD) and an average particle size of 125 micrometers (ProSolv SMCC 90 and ProSolv SMCC 90 HD). The binding agent may be present in any desired amount, including from about 10% to about 40% by weight of the cleansing product. In some aspects the binding agent is present in an amount of from about 20% to about 30% by weight of the cleansing product. In some aspects the binding agent may be present in an amount that is less than the combined weight of all surfactants.

Skin conditioning agent useful in the present invention include aloe extracts, allantoin, bisabolol, ceramides, dimethicone, hyaluronic acid, biosaccharide gum-1, ethylhexylglycerin, pentylene glycol, hydrogenated polydecene, octyldodecyl oleate, dipotassium glycyrrhizate and potassium cetyl phosphate. Emulsifiers may be present in an amount of about 1% to about 10% by weight of the cleansing product, or from about 4% to about 6% by weight of the cleansing product.

Bulking agents may optionally be used in the cleansing products of the present invention. Suitable bulking agents include, for example, corn starch, such as zea may corn starch (sold by Ingredion). When used, bulking agents may be present in an amount of about 3% to about 10% by weight of the cleansing product, or from about 5% to about 8% by weight of the cleansing product.

The present invention also includes a buffering agent. In desired embodiment, the present invention includes two distinctly different buffering agents. The first buffering agent is basic in nature, while the second buffering agent is acidic in nature. One example of a suitable first buffering agent includes sodium bicarbonate, and an example of a suitable second buffering agent includes citric acid. Buffering agents may be used in combined weights of from about 10% to about 50% by weight of the cleansing product, or from about 16% to about 48% by weight of the cleansing product, or from about 34% to about 48% by weight of the cleansing product. It is most desirable that more than one different buffering agent be used, where the first buffering agent is present in an amount that is substantially the same weight amount as the second buffering agent. In some aspects, the first buffering agent may be present in an amount of from about 5% to about 25% by weight of the cleansing product, and the second buffering agent may be present in an amount of from about 5% to about 25% by weight of the cleansing product. As used herein, the term "substantially the same weight amount" means that the first buffering agent and the second buffering agent do not differ in weight amount from each other by more than about 5%. The first buffering agent and second buffering agent may be present in weight ratios of from 1:1 to 10:1, or from 1:1 to 5:1, or from 1:1 to 3:1, respectively. Preferably, the buffering agent and second buffering agent may be present in weight ratios of 1:1.

The total weight amount of all surfactants and all buffering agents may be from about 58% to about 80% of the total weight of the cleansing product. In some aspects, the total weight amount of the surfactants and buffering agents in the cleansing product may be from about 60-70% by weight of the total cleansing product.

In embodiments where the cleansing product is in the form of a pressed tablet, it is desired to include a glidant, which improves the flowability of the powders and aids in the processing of the tablet. Glidants promote the flow of granules or powders by reducing the friction between powders. Glidants may be present in an amount of from about 0.1% to about 2% by weight of the cleansing product, or from about 0.5% to about 1% by weight of the cleansing product. Examples of glidants include, for example, magnesium stearate, fumed silica, starch and talc. The pressed cleansing tablet may additionally include a lubricant, such as magnesium stearate, which prevents adhesion of the tablet.

The cleansing product may include an anticaking agent, which is an additive in cleansing powder to prevent the formation of agglomerated materials and to improve flow during formation of the final product, as well as for easing packaging, transport, and consumption. Some anticaking agents are soluble in water, while others are soluble in alcohols or other organic solvents. They function either by absorbing excess moisture or by coating particles and thereby making them repel water more effectively. Suitable anticaking agents include, for example, celluloses and starches. When used, the anti-caking agent may be present in an amount of from about 3% to about 12% by weight of the cleansing product, and may be from about 1% to about 20% by weight of the cleansing product.

The cleansing product may include colorants and/or fragrances as desired. When used, colorants may be used in an amount of from about 0.1% to about 2% by weight of the cleansing product. In some aspects, the cleansing product may include multiple colorants, and in some aspects, the cleansing product may be a pressed tablet that has distinct layers of colors or includes a color scheme in which the product includes lines or layers of colors. The cleansing product may include a fragrance, where when used, the fragrance is used in an amount of from about 0.01% to about 0.5% by weight of the cleansing product. The cleansing product may be free of added colorants or added fragrances.

The cleansing product may include one or more additional active agents, such as anti-acne agents, anti-aging agents, antimicrobial agents, and the like. Such skin benefit ingredients/carriers include, for example, one or more of the following ingredients: retinol, retinyl esters, tetronic acid, tetronic acid derivatives, hydroquinone, kojic acid, gallic acid, arbutin, ct-hydroxy acids, niacinamide, pyridoxine, ascorbic acid, vitamin E and derivatives, aloe, salicylic acid, benzoyl peroxide, witch hazel, caffeine, zinc pyrithione, fatty acid esters of ascorbic acid, colloidal oatmeal, acids such as alpha hydroxy acid, polyhydroxy acid, and beta hydroxy acid, enzymes such as chlorella, papaya, and papain, N-acetylglucosamine, and gluconolactone. Other skin care ingredients and carriers are known to those of skill in the art and may be used in the compositions of the invention.

Additional skin benefit ingredients that may be included in the composition of the invention include one or more of the following ingredients: emulsifying agent such as potassium cetyl phosphate, glyceryl stearate and PEG-100 stearate; conditioning agents, such as polyquaterniums, cotton powder and panthenol; pearlizing agents, such as glycol distearate, distearyl ether, and mica; UV filters, such as octocrylene, octyl methoxycinnamate, benzophenone-4, titanium dioxide, and zinc oxide; exfoliation additives, such as apricot seeds, walnut shells, polymeric or cellulose beads, and pumice; silicones such as dimethicone, cyclomethicone, and amodimethicone; moisturizing agents such as petrolatum, sunflower oil, fatty alcohols, glucose, ceramides, hyaluronic acid, lactic acid, gelatin, ascorbic acid, allantoin, milk protein, maltodextrin, zinc gluconate, urea and shea butter; foam stabilizers such as cocamide MEA and cocamide DEA; anti-bacterial agents such as triclosan; humectants such as glycerin; thickening agents such as guar sodium chloride, and carbomer; hair and skin damage repair agents such as proteins, hydrolyzed proteins, and hydrolyzed collagen; foam boosters such as cocamide MIPA; preservatives such as phenoyethanol, ethylhexyl glycerin, sodium benzoate, and formaldehyde donors; and fragrances. If used, the additional skin benefit agent is preferably an emulsifying agent such as potassium cetyl phosphate and it is in an amount from about 1% to about 10%, more preferably from about 2 to about 5%.

It may be desired that the final product include one or more superdisintegrants. For example, the product may include Ac-Di-Sol® Croscarmellose Sodium, which is an internally cross-linked sodium carboxymethyl cellulose (NaCMC) that aids in the disintegration and dissolution of pharmaceutical and dietary supplement tablets, capsules, and granules. If used, a superdisintegrant may be used in an amount of from about 0.01 to about 2% by weight of the final product, or about 0.1 to about 1% by weight of the final product.

As discussed above, the cleansing product may be in any solid form, and in some embodiments, it is desirable that the cleansing product be in the form of a pressed tablet or a loose powder. When a pressed tablet is used, the pressed tablet should have the right balance between compression, friability and dissolution times. The pressed tablet desirably is compressed so that it maintains the shape and feel of a tablet, but allows for a user to break or crush the tablet to reduce the tablet to a powdered or granulated form. The pressed tablet desirably has a friability level that allows it to be crushed by a user, but not so easily friable that it cannot retain its shape when packaged and shipped to users.

The cleansing product is packaged in a substantially water-tight package and desirably is in an air-tight package. For example, the product may be contained within its own single-use packaging, such as a sachet, a capsule, a dissolvable film, a blister package, or other single-wrapped or sealed environment. The user releases the cleansing product from its packaging for use, such as by unwrapping or releasing it from a blister package, or separating/breaking a capsule, or dissolving an outer film. In embodiments where the product is a tablet, it is desired that the user break the tablet apart to form a broken tablet. For example, this may be achieved by crushing the tablet with the user's hands or with a crushing tool, or the tablet may be crushed by twisting the tablet in the user's fingers. In some aspects, the tablet may be crushed through a combination of hand and finger use, such as by placing the tablet within the palm of the user's hand and then using a finger or thumb to crush the tablet within the palm of the user's hand.

In aspects where the cleansing product is in the form of a powder, the user may not need to manipulate the cleansing product to render it more broken apart.

Once crushed or dispensed in the form of a powder, the user may add a small amount of water to the cleansing product (e.g., about 3-10 mL, or about 3-5 mL), and run the wetted cleansing product within the user's hands, fingers, body, face, or hair. By running the wetted product within the user's hands, fingers, body, face or hair, the wetted product forms a foamed cleansing product. The product has the foaming generation rate described below, and desirably within about 2 to about 5 seconds after exposure to water and rubbing within the user's hands, fingers, body, face or hair, at least about 95% of the solid cleansing product becomes a foamed cleansing product. The user then can apply the foamed cleansing product to the area or areas of the user's body as desired, including hands, body, face, or hair. When cleansing is complete, the user may rinse the foamed and applied cleansing product with water.

The present invention includes a method of making a solid cleansing product in the form of a pressed tablet As mentioned above, it is desired that the components of the pressed tablet be in the form of powders, and therefore if desired or if necessary, the method of forming a tablet may include an initial step of rolling or milling individual components into the form of a powder. For example, the first step may be to roll or mill the one or more surfactants into a powder having a particle size of less than about 2 microns in cross-sectional diameter or less than about 1.1 microns in cross-sectional diameter. By way of example, a first surfactant may initially be in the form of flakes and the second surfactant may be in the form of noodles, but each of these surfactants are milled (either together or individually) to form a powder having a desired particle size.

When making a cleansing product described herein, the surfactant (or surfactants, if used) are added to a dry powder blender, such as a LM-40 Blender (manufactured by L. B. Bohle). To the surfactant(s) is added a mixture of other dry components except for the glidant. For example, the mixture of other dry components may include the binding agent(s), bulking agent(s), buffering agent(s), anti-caking agent(s), and other optional components (such as anti-acne agents, colorants, fragrances). These components are then mixed in the Blender for a sufficient time to achieve thorough mixing, which may be about 10 minutes at about 25-50 RPM, or until fully mixed. At the conclusion of this initial mixing stage, the glidant(s) may then be added to the mixture if desired, and the composition with glidant(s) may then be mixed for an additional 5 minutes at about 25-50 RPM, or until fully mixed. Once mixed, the composition is ready for tableting, if the final product is to be made into a tablet.

In embodiments where it is desired that the product be in the form of a tablet, the mixed composition is added to a tableting device, where it is subjected to the force and compression desired to form a suitable tablet which will be suitable for packaging and dispensing, but will also be capable of being used (and crushed, if desired) by a user. The powdered materials may be subjected to a compression force of about 2.0 kN to about 5.0 kN, with an ejection force of about 70 N to about 120 N. The pressed tablet desirably has a weight of about 900 to about 1100 mg, and more desirably about 950 mg to about 1010 mg. The pressed tablet desirably has an average hardness of about 1.0 kp to about 5.0 kp, and more desirably about 1.2 kp to about 3.5 kp. Finally, although the tablet may have any desired thickness, in some aspects it may have a thickness of about 5 mm to about 10 mm, or from about 6 mm to about 8 mm. The final tablet may have any shape desired, including for example a circle, square, hexagon, or other cross-sectional shape, or may be a sphere or cylinder with any desired cross-sectional shape.

The final product, whether in the form of a tablet, or a loose powder, or in any other form, may be packaged in a suitable container. It is desired that the container be substantially air-tight, and more desirably the container is fully air-tight. Once the cleansing product is formed and packaged, it can be distributed to a user or users, and the product may be used by the user as he or she wishes. In addition to providing a cleansing function, the cleansing product may additionally include one or more components to provide other benefits, such as anti-aging or anti-wrinkle benefits.

As discussed above, the present invention provides a foamable cleansing product, which is suitable for use directly on the user's skin, hair or face. It is desirable that the cleansing product generates a suitable foam volume, a suitable level of foam stability, and the foam should have a soft, cushiony feel, which may be measured by the bubble size or bubble size distribution after a foam is produced. As used herein, "Foam Volume" refers to the volume of foam generated when the cleansing product is exposed to added water and agitated by the user or by an instrumental method. "Peak Foam Volume" refers to the maximum volume of foam generated during a predetermined agitation time, and immediately thereafter the foam begins to decay and lessen. Further, as used herein, "Foam Decay" refers to the percent loss in foam volume relative to the foam volume at the end of agitation for a predetermined length of time. In use by a consumer, the end of agitation is defined as the point where the product has been combined with water and manipulated by the user (e.g., through rubbing in hands or on skin) to a sufficient point where the foam is generated to a sufficient level. This may be after about 10 seconds of agitation, about 15 seconds of agitation, about 20 seconds of agitation or about 30 seconds of agitation by a user. For the SITA foam test, defined below, agitation is from the propeller pulsed 13 fifteen-second intervals, so that the total agitation time is 195 seconds. Therefore, for the SITA foam test, the "end of agitation" is after this 195 second agitation period. Foam generation time, Foam Volume, Peak Foam Volume, and Foam Decay are based upon the instrumental foam test method and, less quantitatively, to the aesthetic evaluations described below.

Initial screening of example formulations involved aesthetic evaluations during intended usage of the product. The product desirably has a foam generation time of about 2-5 seconds, which means that the product begins foaming within about 2 to about 5 seconds after exposure to water and agitation once it is in the form of a powder or crushed product, whether the product is dispensed as a powder or dispensed as a tablet that is crushed by the user. Agitation may include the user rubbing the product (e.g., in the user's hands, on the user's face, or on the user's body). Foam generation time refers to the time required for at least about 95% of the product to react with the water and form a foam. For testing purposes, the Peak Foam Volume and Foam Decay were evaluated quantitatively through the instrumental foam test method described below.

The instrumental foam test method used to quantitatively compare Example formulations was the "SITA Foam Test" which was performed as follows: foam was generated and measured through the use of a SITA Foam Tester R-2000 (sold by SITA Messtechnik GmbH). The SITA Foam Test protocol consists of two phases, both of which are temperature controlled at 30±2 degrees C. The first phase involves "Foam Generation" during which 0.25 gram of test product in 250 mL of moderately hard water (100 ppm $CaCl_2$)) are subjected to thirteen 15-second propeller pulses at 1200 RPM with Foam Volume measurements taken after each pulse (measurements take 10 or less seconds). After the foam from the thirteenth pulse is measured, the "Foam Decay" phase begins for assessing foam stability. "Foam Decay" involves Foam Volume measurements every 60 seconds for 15 minutes. Good foamers generate at least 300 mL of foam during the "Foam Generation" phase and stable foams decay less than 10% in volume during the 10-minute "Foam Decay" phase. The SITA Foam Test measures incremental Foam Volume during the Foam Generation phase, measures the Peak Foam Volume, and measures incremental Foam Volume during Foam Decay phase.

As used herein, the term "Foam Decay" refers to the amount of reduction in Foam Volume which takes place from the time that the Foam Generation phase ends to 10 minutes later. For example, if a product has a Foam Volume at the end of the Foam Generation phase of 300 mL, and is reduced to 270 mL after 10 minutes, its Foam Decay was 10%. It is desirable that the formulation herein have a Foam Decay value of 10% or less, or of 8% or less, or of 5% or less.

The cleansing products herein may be packaged in any desired method or packaging, which may be dependent upon the particular form of the cleansing product. For example, a pressed tablet may be packaged in a container including a plurality of pressed tablets. Alternatively, a pressed tablet may be packaged in a blister package, whereby the user can dispense one pressed tablet at a time and the remaining tablets may be securely stored in a water-tight or an air-tight blister package. If the cleansing product is in the form of a flowable powder, the cleansing product may be stored in a single-use, air-tight package or sachet, or may be stored in a container (such as a tube, canister, bottle, or ampoule) whereby a desired amount of cleansing product can be dispensed by the user as needed. Put another way, the product may be stored in a multi-use container, where the user takes a desired amount of product for use, or the product may be stored in single-use containers, whereby the package dispenses a single amount of cleansing product upon opening the container.

EXAMPLES

Through the below non-limiting examples, the present invention may be more fully understood. In the below examples, the product was formed (as a powder) and was subject to evaluation within a laboratory setting. After formation of the product, the product was tested informally for aesthetics, such as foaming, skin feel, time to foam, dissolving profile of the components, and dryness after use. In addition, for some of the examples below, attempts were made to form a tablet as described above. If the product did not pass the initial evaluation, either through aesthetic look and feel or through failed tablet making, it was considered to fail and was not tested for additional foam properties. If the product passed the initial evaluation, including either aesthetic test and/or tablet making test, it was subjected to the Foam Test, described herein.

Foaming profiles for two commercial liquid cleansing products were evaluated to give comparative levels of foam as shown in FIG. 1. A first liquid cleanser (NEUTROGENA™ Oil-Free Acne Wash) was found to generate greater than 700 mL of Peak Foam Volume, while a second liquid cleanser (NEUTROGENA' Ultra Gentle Daily Cleaner) provided about 300 mL of Peak Foam Volume. It is desired that the solid cleansing products described herein have a Peak Foam Volume of about 300 mL or greater.

The formulations tested are described in the Examples below, and the detailed formulations are described in the Tables below, with the amount listed being the weight percent of the final formulation. Based upon the Examples described herein, the sulfate-free formulation containing a nonionic surfactant, such as Sodium cocoyl isethionate, combined with a secondary surfactant provides sufficient amount of foam in the presence of magnesium sulfate and buffering agents. In addition, formulations showed better performance if the secondary surfactant is Cocamidopropyl Betaine or Sodium Methyl Cocoyl Taurate, or Cocamidopropyl Betaine combined with Sodium Methyl Cocoyl Taurate, with a higher weight fraction of Cocamidopropyl Betaine. Surprisingly, the formulations where the secondary surfactant is anionic suffered in terms of Foam Volume and Foam Stability performance.

Example 1

Figure 2:
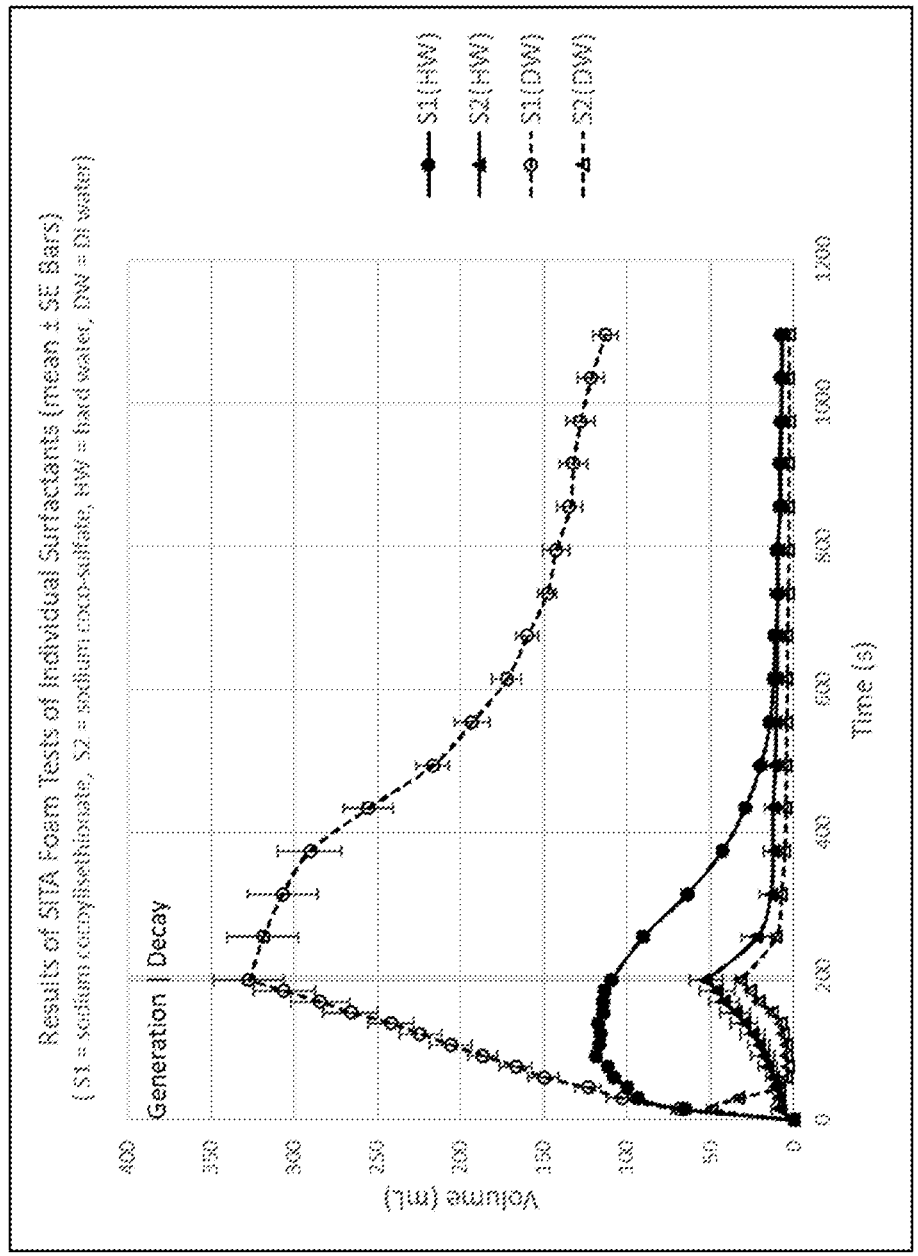
FIG. 2 is a graph showing foam test results for surfactants tested.

Sodium Cocoyl isethionate and a sulfate-containing surfactant (sodium coco sulfate) were each tested individually in differing water types, to determine foaming levels and stability. Formula 51 included only sodium cocoyl isethionate, while Formula S2 included only sodium coco sulfate (each in an amount of about 9% in a full formulation). Each was subjected to the SITA Foam Test, but each was tested in hard water (100 ppm CaCl2), and each was tested in DI water. The results are shown in FIG. 2.

As can be seen, the sodium cocoyl isethionate provided higher Peak Foam Volume and slightly better Foam Decay (in hard water). The sodium coco sulfate by itself performed poorly in both hard water and in DI water.

Surprisingly, however, the sodium cocoyl isethionate by itself in DI water performed quite well, reaching a Peak Foam Volume of about 325 mL. Its stability began to suffer after a couple of minutes, but was still higher than the sodium cocoyl isethionate in hard water. It would have been expected that sodium coco sulfate would provide a higher Foam Volume, since anionic surfactants typically provide better foaming than nonionic surfactants due to the presence of charge to promote electrostatical repulsion.

Examples A-D

Given the foaming profile of sodium cocoyl isethionate, various example compositions were prepared including sodium cocoyl isethionate as the first surfactant. Examples A-D were prepared, each including sodium cocoyl isethionate as the first surfactant, but including different non-sulfate containing surfactants as the second surfactant. Detailed formulations are set forth in the Table 1 below. As can be seen, for each of the Examples, the first surfactant is present in a weight percentage of 9%, and in each of the Examples, the weight percentage of the active second surfactant component is also 9%.

TABLE 1

| Component | | Examples A-D | | | |
|---|---|---|---|---|---|
| | | Example | | | |
| (% active) | Function | A | B | C | D |
| Sodium Cocoyl isethionate | First Surfactant | 9.0% | 9.0% | 9.0% | 9.0% |
| Sodium Lauroyl Sarcosinate (95%) | Second Surfactant | 9.47% | — | — | — |
| Cocamidopropyl Betaine (84.5%) | Second Surfactant | — | 10.65% | — | — |
| Sodium Dioctyl Sulfosuccinate (85%) | Second Surfactant | — | — | 10.59% | — |
| Sodium Methyl Cocoyl Taurate | Second Surfactant | — | — | — | 9.00% |
| Potassium Cetyl Phosphate | Emulsifying Agent | 2.0% | 2.0% | 2.0% | 2.0% |
| Sodium Bicarbonate | First Buffering Agent | 24.0% | 24.0% | 24.0% | 24.0% |
| Citric Acid | Second Buffering Agent | 24.0% | 24.0% | 24.0% | 24.0% |
| Lactose Monohydrate | Binding Agent | 30.03% | 28.85% | 28.91% | 30.50% |
| Magnesium Stearate | Lubricant | 1.0% | 1.0% | 1.0% | 1.0% |
| Silica | Flowing Agent | 0.5% | 0.5% | 0.5% | 0.5% |

Figure 3:
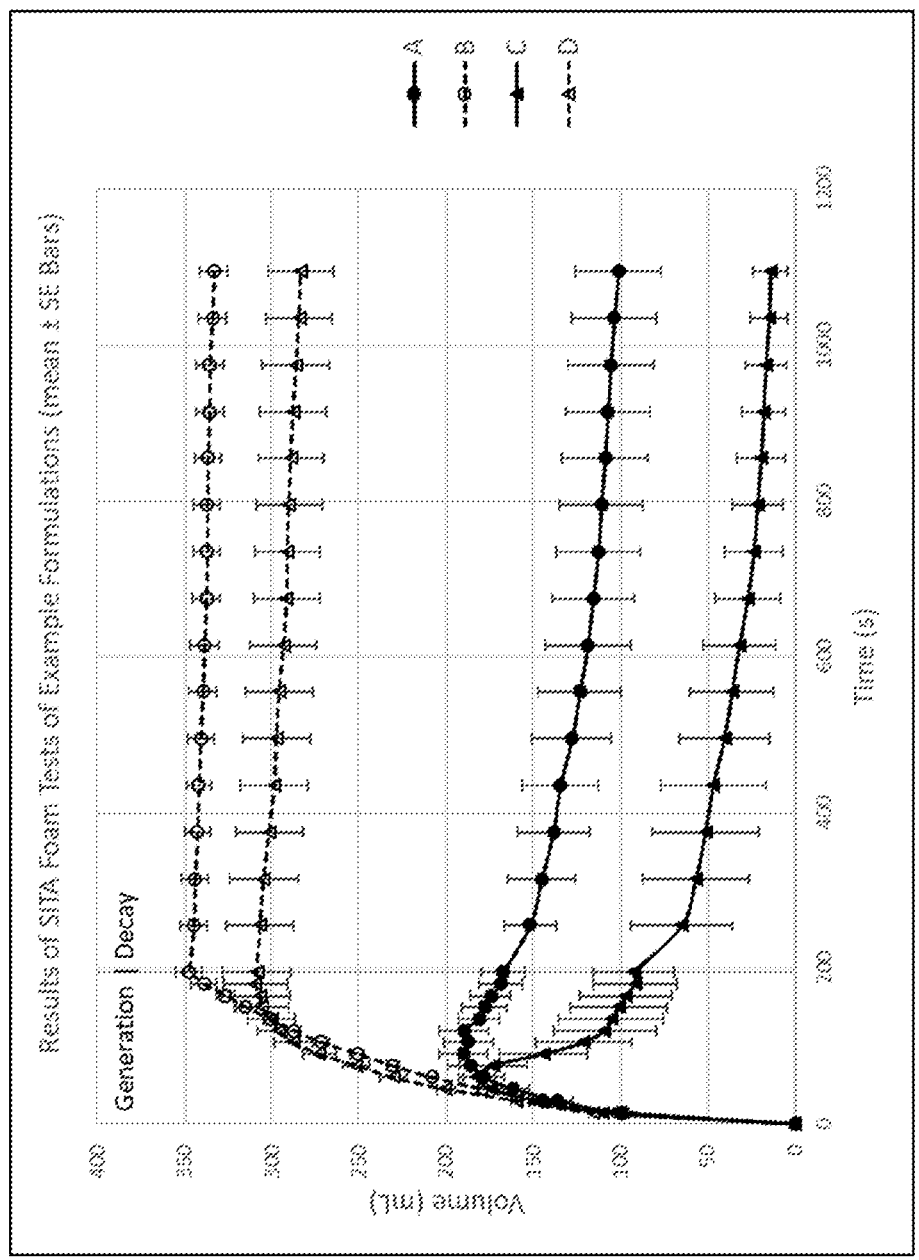
FIG. 3 is a graph showing foam test results for various tested formulations.

Each of Examples A-D were tested using the SITA Foam Test. Results are shown in FIG. 3. As can be seen, the sulfate-free formulations including sodium cocoyl isethionate and, as a second surfactant, cocamidopropyl betaine and sodium methyl cocoyl taurate showed adequate Peak Foam Volume and adequate Foam Decay. In contrast, the combination of sodium cocoyl isethionate and, as a second surfactant, sodium lauroyl sarcosinate and sodium dioctyl sulfosuccinate were inadequate in foaming profile. Example A demonstrated a Peak Foam Volume of only approximately 185 mL and decayed quickly over time. Example C reached a Peak Foam Volume of only about 175 mL, and decayed even more quickly over time. Example D reached a Peak Foam Volume above 300 mL and maintained its foam over time with an acceptable Foam Decay of 6% in 10 minutes. Example B reached a Peak Foam Volume at around 350 mL and had a Foam Decay of only 3% in 10 minutes.

This demonstrates that not all combinations of sodium cocoyl isethionate plus a second non-sulfate surfactant are successful.

Examples E-G

Given the foaming profiles of the formulations including, as a secondary surfactant, sodium methyl cocoyl taurate and cocamidopropyl betaine, three additional sulfate-free formulations were prepared and tested for foaming properties with all three surfactants in varying ratios. The additional formulations are Examples E-G, set forth below.

TABLE 2

Examples E-G

| Component (% active) | Function | Example E | Example F | Example G |
|---|---|---|---|---|
| Sodium Cocoyl isethionate | First Surfactant | 9.0% | 9.0% | 9.0% |
| Cocamidopropyl Betaine (84.5%) | Second Surfactant | 5.33% | 7.10% | 3.55% |
| Sodium Methyl Cocoyl Taurate | Third Surfactant | 4.5% | 3.0% | 6.0% |
| Potassium Cetyl Phosphate | Emulsifying Agent | 2.0% | 2.0% | 2.0% |
| Sodium Bicarbonate | First Buffering Agent | 24.0% | 24.0% | 24.0% |
| Citric Acid | Second Buffering Agent | 24.0% | 24.0% | 24.0% |
| Lactose Monohydrate | Binding Agent | 29.68% | 29.4% | 29.95% |
| Magnesium Stearate | Lubricant | 1.0% | 1.0% | 1.0% |
| Silica | Flowing Agent | 0.5% | 0.5% | 0.5% |

As can be seen, Example E includes the first surfactant in an active weight percent of 9%, the second surfactant and third surfactants each in active weight percentages of 4.5%. Example F includes the first surfactant in an active weight percent of 9%, the second surfactant in an active weight percent of 6%, and the third surfactant in an active weight percentage of 3%. Example G includes the first surfactant in an active weight percent of 9%, the second surfactant in an active weight percent of 3%, and the third surfactant in an active weight percentage of 6%.

Figure 4:
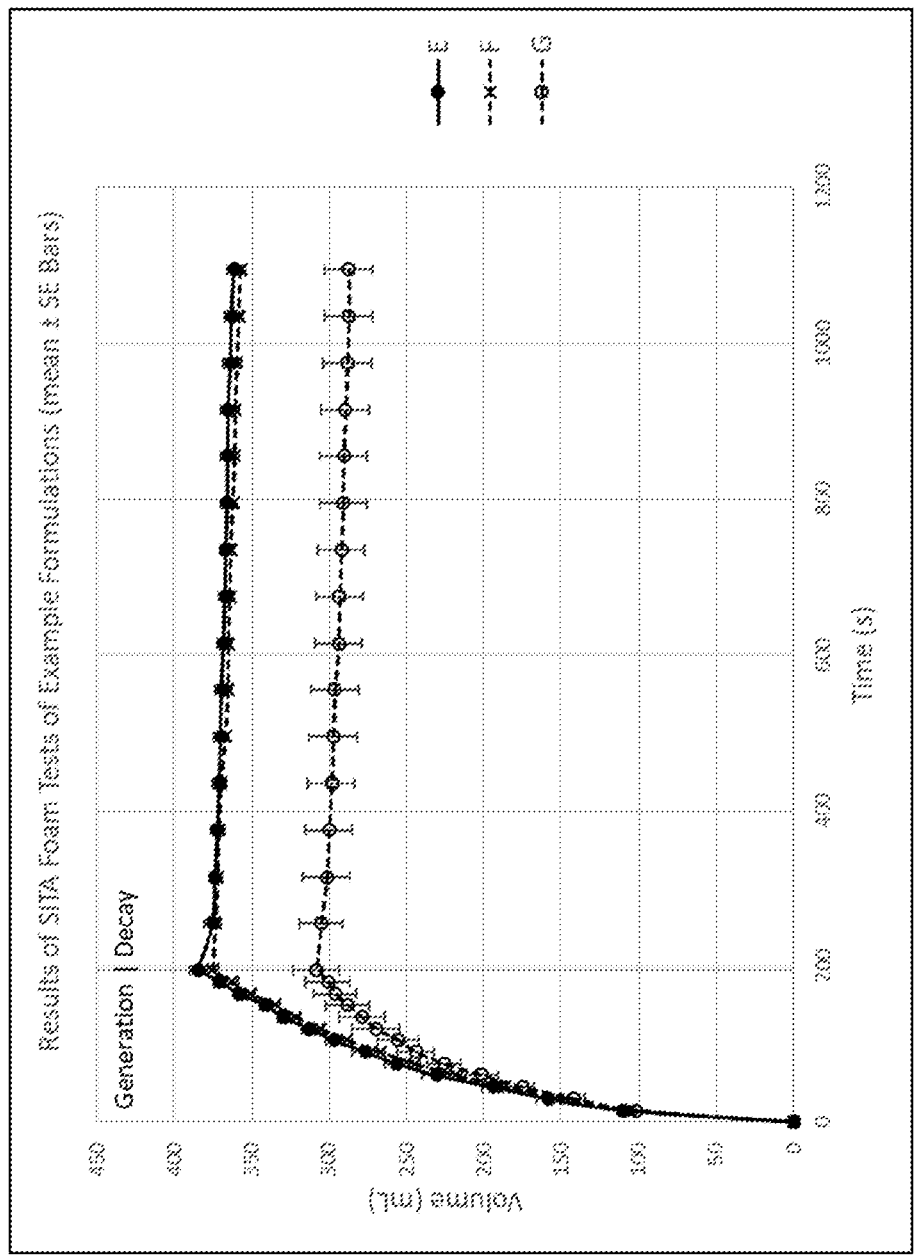
FIG. 4 is a graph showing foam test results for various tested formulations.

Each of Examples E-G were subjected to the SITA Foam Test, and the results are shown in FIG. 4. As can be seen, Examples E and F demonstrated superior foaming profiles, with high Peak Foam Volumes of 375 mL and Foam Decay less than 5% in 10 minutes. Example E was slightly better than Example F, but both were substantially similar. Although Example G produced a Peak Foam Volume slightly above 300 mL, it demonstrated a statistically significant lower foaming level than Examples E and F. All three products demonstrated acceptable foam stability.

This test demonstrates that when three surfactants are used in a solid foaming cleanser (each including sodium cocoyl isethionate), when cocamidopropyl betaine is present in an active weight percentage greater to or equal to the sodium methyl cocoyl taurate, the foaming level is greater than when cocamidopropyl betaine is present in a lower active weight percentage than sodium methyl cocoyl taurate. In addition, the combination of cocamidopropyl betaine and sodium methyl cocoyl taurate provided greater foaming levels in combination as compared to when used as the second surfactant individually. It was surprising that the combination of cocamidopropyl betaine and sodium methyl cocoyl taurate produced slightly more foam than the cocamidopropyl betaine and sodium methyl cocoyl taurate alone in combination with sodium cocoyl isethionate since anionic surfactants typically demonstrate the highest foam formation.

Further, when comparing the previous Example to the current Example, it was found that the lower foaming level demonstrated when sodium methyl cocoyl taurate was double the amount of cocamidopropyl betaine was nearly identical to the foaming level when sodium methyl cocoyl taurate was used by itself as the second surfactant. This demonstrates that removing a part of the sodium methyl cocoyl taurate and replacing with cocamidopropyl betaine does not improve the foaming level when sodium methyl cocoyl taurate is used by itself (as the second surfactant). When the amount of cocamidopropyl betaine was increased to be equal to or more than sodium methyl cocoyl taurate, the foaming level significantly increased.

The invention claimed is:

1. A solid cleansing product comprising:
   a. At least a first surfactant present in a first surfactant weight amount and at least a second surfactant present in a second surfactant weight amount, both of the first surfactant and the second surfactant being free of sulfate-containing materials, wherein the first surfactant weight amount and the second surfactant weight amount are approximately equal to each other, wherein the combined weight amount of the first surfactant and the second surfactant is about 16% to about 20% by weight of the solid cleansing product, and wherein the first surfactant is an isethionate and the second surfactant is a betaine; and
   b. At least a first buffering agent and at least a second buffering agent, wherein the first buffering agent and the second buffering agent are present in a combined buffering agent weight amount;
      Wherein the combined buffering agent weight amount is at least double the combined weight amount of the first surfactant and the second surfactant; and
      wherein the combined weight amount of the first and second surfactants and the first and second buffering agents is from about 60% to about 70% by weight of the solid cleansing product.

2. The solid cleansing product of claim 1, wherein the combined buffering agent weight amount is at least 2.5 times the combined weight amount of the first surfactant and the second surfactant.

3. The solid cleansing product of claim 1, wherein the combined weight amount of the first surfactant and the second surfactant is about 18% by weight of the solid cleansing product.

4. The solid cleansing product of claim 1, wherein the combined buffering agent weight amount is about 36% to about 48% by weight of the solid cleansing product.

5. The solid cleansing product of claim 1, wherein the combined buffering agent weight amount is about 48% by weight of the solid cleansing product.

6. The solid cleansing product of claim 1, wherein the first buffering agent is a basic buffering agent.

7. The solid cleansing product of claim 1, wherein the second buffering agent is an acidic buffering agent.

8. The solid cleansing product of claim 1, wherein the cleansing product has a foam peak of greater than 300 mL, as measured by using 0.25 g of cleansing product and 250 mL of water in a SITA Foam Tester.

9. The solid cleansing product of claim 1, wherein the cleansing product has a foam decay of less than 10% at 10 minutes after the end of agitation time.

10. The solid cleansing product of claim 1, wherein the solid cleansing product is in the form of a loose powder.

11. A solid cleansing product comprising:
   a. A first surfactant present in a first surfactant weight amount, a second surfactant present in a second surfactant weight amount, and a third surfactant present in a third surfactant weight amount, each of the first, second and third surfactants being free of sulfate-containing materials, wherein the first surfactant weight amount is approximately equal to the combined weight amount of the second surfactant and the third surfactant, wherein the second surfactant weight amount is approximately equal to the third surfactant weight amount, wherein the first surfactant is an isethionate, the second surfactant is a betaine, and the third surfactant is a taurate; and
   b. At least a first buffering agent and at least a second buffering agent, wherein the first buffering agent and the second buffering agent are present in a combined buffering agent weight amount;
      wherein the combined buffering agent weight amount is at least double the combined weight amount of the first surfactant and the second surfactant; and
      wherein the combined weight amount of the first, second and third surfactants and the first and second buffering agents is from about 60% to about 70% by weight of the solid cleansing product.

12. The solid cleansing product of claim 11, wherein the cleansing product has a foam peak of greater than 300 mL, as measured by using 0.25 g of cleansing product and 250 mL of water in a SITA Foam Tester.

13. The solid cleansing product of claim 1, wherein the first surfactant and second surfactant are present in a weight ratio of from 1:1 to about 1:1.5.

14. A solid cleansing product comprising:
   A first surfactant present in a first surfactant weight amount, a second surfactant present in a second surfactant weight amount, and a third surfactant present in a third surfactant weight amount, each of the first, second and third surfactants being free of sulfate-containing materials, wherein the first surfactant weight amount is approximately equal to the combined weight amount of the second surfactant and the third surfactant, wherein the second surfactant weight amount is approximately double the third surfactant weight amount, wherein the first surfactant is an isethionate, the second surfactant is a betaine, and the third surfactant is a taurate; and
   a. At least a first buffering agent and at least a second buffering agent, wherein the first buffering agent and the second buffering agent are present in a combined buffering agent weight amount;
   wherein the combined buffering agent weight amount is at least double the combined weight amount of the first surfactant and the second surfactant; and
   wherein the combined weight amount of the first, second and third surfactants and the first and second buffering agents is from about 60% to about 70% by weight of the solid cleansing product.

15. The solid cleansing product of claim 14, wherein the cleansing product has a foam peak of greater than 300 mL, as measured by using 0.25 g of cleansing product and 250 mL of water in a SITA Foam Tester.

* * * * *